US006258986B1

(12) United States Patent
Klingler et al.

(10) Patent No.: US 6,258,986 B1
(45) Date of Patent: *Jul. 10, 2001

(54) PROCESS FOR THE PRODUCTION OF DINITROTOLUENE

(75) Inventors: Uwe Klingler, Dormagen; Thomas Schieb, Rösrath; Dietmar Wastian, Dormagen; Gerhard Wiechers, Leverkusen, all of (DE); Jürgen Zimmerman, Walnut Creek, CA (US)

(73) Assignee: Bayer Aktiengesellschaft, Leverkusen (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/511,028

(22) Filed: Aug. 3, 1995

(30) Foreign Application Priority Data

Aug. 11, 1994 (DE) ................................. 44 28 461

(51) Int. Cl.⁷ ...................................... C07C 205/00
(52) U.S. Cl. ......................... 568/934; 568/932; 568/927
(58) Field of Search .................... 568/934, 932, 568/927

(56) References Cited

U.S. PATENT DOCUMENTS 4,021,498  5/1977  Alexanderson et al. ............. 260/645
4,663,490  5/1987  Gerken et al. ........................ 568/934
5,345,012  *  9/1994  Schieb et al. ........................ 568/934

OTHER PUBLICATIONS

R.A. Vauck, H. A. Müller, Grundoperationen chemischer Verfahrenstechnik, (Basic Chemical Process Engineering Operations) 5th edition VEB Leipzig (month unavailable) 1962, p. 447.

Ullmanns Encyklopädie der technischen Chemie (Encyclopedia of Industrial Chemistry) 4th edition, vol. 17, paged 392, 1979.

* cited by examiner

*Primary Examiner*—Dwayne C. Jones
(74) *Attorney, Agent, or Firm*—Joseph C. Gil; Lyndanne M. Whalen

(57) ABSTRACT

Dinitrotoluene is produced by nitrating toluene with nitrating acid under adiabatic conditions in a manner such that some mononitrotoluene is present in reaction mixture. The nitration reaction mixture is then treated to remove at least 5% by weight of water before the reaction mixture is separated into an acid phase and an organic phase. The product dinitrotoluene is recovered from the organic phase. The acid phase may be recycled after nitric acid has been added to replace that which was used in the nitration reaction.

10 Claims, No Drawings

PROCESS FOR THE PRODUCTION OF DINITROTOLUENE

BACKGROUND OF THE INVENTION

The present invention relates to the production of dinitrotoluene by toluene nitration with nitrating acid under adiabatic conditions.

It is known to convert toluene to dinitrotoluene (DNT) adiabatically (EP-A 597,361). Toluene is reacted adiabatically with at least 2 equivalents of a nitrating acid satisfying specific compositional requirements. A final temperature greater than 120° C. is reached. After phase separation at this temperature, the acid phase is reconcentrated (flash evaporation under vacuum). The heat of the acid phase is used for the reconcentration. The reconcentrated acid is made up with nitric acid and is recycled to the process.

An inherent difficulty in this process is the passage of a certain amount of DNT which is dissolved in the acid with the water which distills off in the flash evaporation. This residual DNT solidifies under the water condensation conditions (the isomer mixture solidifies at approximately 55° C.) and fouls the heat exchanger. There are two possible solutions to this problem.

In one of the possible solutions, staggered heat exchangers may be used. These staggered heat exchangers are operated alternately. When some of the exchangers have been fouled, they are idled and the alternate exchangers are used. The DNT present in the fouled exchangers is then melted off while those exchangers are idle. Fouling of exchange surfaces results in rapid deterioration in cooling performance. Frequent changeovers are therefore necessary. Extra power is required to melt the DNT from the idle condenser (heating up and cooling).

In a second possible solution to the problem of fouling, the heat exchanger, a co-condenser or injection condenser may be used to condense solid-forming exhaust vapors (R. A. Vauck, H. A. Muller, *Grundoperationen chemischer Verfahrenstechnik* [Basic Chemical Process Engineering Operations], 5th edition, VEB Leipzig 1962, p. 447). In this process, the exhaust vapors are introduced into a cold water jet spray and DNT is segregated in finely divided form as a solid. Co-current and counter-current operation are possible. Because of the large volumes of water required in this procedure, the water is circulated in a loop and cooled in the return branch. In order to separate the DNT from the water, a portion of the flow is passed out through a lock. This increases the risk of blocking lines and nozzles with low-melting organic components which tend to adhere to such lines and nozzles. Recovery of DNT in pure form requires a significant amount of energy because the DNT must first be melted down before it is recovered.

A considerably simpler and more elegant solution to the problem of fouled heat exchangers is an isothermal two-stage production of dinitrotoluene such as that disclosed in Ullmann, *Encyklopädie der technischen Chemie* [Encyclopedia of Industrial Chemistry], 4th edition, vol. 17, p. 392, Verlag Chemie, Weinheim (1979). In this two-stage process, an isomeric mixture of mononitrotoluene (MNT) is first prepared. This isomeric mixture is converted in a second, separate process step to an isomeric mixture of dinitrotoluene. The problem of fouling of the heat exchanger when reconcentrating the spent acid under vacuum is eliminated by injecting MNT from the first stage into the exhaust vapors (DE-A 3,409,719). The MNT which is injected lowers the melting point of the DNT thereby ensuring that the exhaust vapors remain fluid even under the water condensation conditions. The organic phase which is isolated by phase separation is recycled into the reaction.

This elegant solution is not useful in a single-stage adiabatic process for toluene dinitration (EP-A 597,361) because there is no freely available MNT present in the single-stage process. MNT is a non-isolatable intermediate product in such a single-stage process.

SUMMARY OF THE INVENTION

It is an object of the present invention to provide a continuous, single-stage adiabatic process for the production of dinitrotoluene.

It is also an object of the present invention to provide a single-stage process for the production of dinitrotoluene in which the problem of fouling heat exchangers is avoided.

It is another object of the present invention to provide a single-stage, adiabatic process for the production of dinitrotoluene in which costly process steps and the use of extra energy are avoided.

These and other objects which will be apparent to those skilled in the art are accomplished by nitrating toluene with a nitrating acid composition satisfying specified compositional criteria under adiabatic conditions in a single stage, removing at least 5% by weight of any water present in the reaction mixture and separating the reaction mixture into an acid phase and an organic phase containing the dinitrotoluene. The acid phase may be recycled after sufficient nitric acid has been added to replace that spent in the nitration reaction.

DETAILED DESCRIPTION OF THE PRESENT INVENTION

The present invention relates to a process for the continuous production of dinitrotoluene isomer mixtures by toluene nitration. In this process, toluene is reacted under adiabatic conditions in a single stage in a continuously operated reactor with a nitrating acid. This nitrating acid is made up of (a) from about 80 to about 100% by weight (based on total weight of nitrating acid) inorganic materials which include: (i) from about 60 to about 90% by weight (based on the total weight of (a)) of sulfuric acid, (ii) from about 1 to about 20% by weight (based on the total weight of (a)) of nitric acid and (iii) at least 5% by weight (based on the total weight of (a)) of water and (b) from 0 to about 20% by weight (based on the total weight of nitrating acid) of organic materials which include at least 70% by weight (based on total weight of (b)) of dinitrotoluene isomers with the remainder being by-products of the nitration process. The toluene and nitrating acid are used in amounts such that the molar ratio of nitric acid to toluene is at least 1.5:1, preferably at least 1.8:1, most preferably at least 1.9:1. This molar ratio is selected so that small quantities of mononitrotoluene are still present in the reaction mixture after the nitration. At least 5% by weight (based on the total reaction mixture) of the water present in the nitration reaction mixture containing dinitrotoluene is removed. This removal may be achieved by distillation, preferably by flash evaporation, optionally with simultaneous supply of heat. The reaction mixture from which water has been removed leaves the reactor continuously at a temperature of at least 120° C. At this point, up to 0.6 mole, preferably up to 0.3 mole, most preferably up to 0.2 mole, of nitric acid (50 to 100% by weight) may optionally be mixed in the nitration reaction mixture. The nitration reaction mixture from which water has been removed is then separated into an upper product phase and a lower acid phase. The product phase is worked up to recover the product dinitrotoluene. The acid phase may be recycled into the beginning of the process after the addition of nitric acid (50 to 100% by weight nitric acid) to replace the nitric acid used during the nitration reaction.

It has surprisingly been found that condensation of the exhaust vapors may be carried out advantageously if the reaction is conducted in a manner such that small amounts of MNT (minimum 5% by weight based on total weight of reaction product) remain in the reaction product. Separation of the organic phase after acid reconcentration (i.e., removal of at least 5% by weight water) also promotes condensation of the exhaust vapors without solidification of the dinitrotoluene. The reaction product containing small quantities of MNT is subjected to reconcentration (i.e., removal of at least 5% by weight water) immediately after leaving the reactor. The MNT present is distilled off with the water and small quantities of DNT at the top. The ratio of MNT to DNT in the exhaust vapor condensate is from about 10:1 to about 1:5, preferably from about 5:1 to about 1:5. This MNT/DNT mixture ensures that the exhaust vapor condensate runs out as a fluid under the water condensation conditions at the heat exchangers.

The surprising feature is that virtually all of the MNT distills off with the exhaust vapors in the reconcentration step, so that the quantity of MNT which remains in the distillation bottom is very small, and the DNT yield is reduced only slightly. The MNT/DNT mixture which passes over with the exhaust vapors is separated and recycled into the reaction.

This outcome is all the more surprising because process engineering calculations predict significantly higher quantities of residual SNT in the bottom than those which are actually obtained.

The nitration product is completely free of MNT if, after the reconcentration step, small quantities of 50 to 100% by weight nitric acid, optionally with simultaneous utilization of a mixing unit, are added to the reaction mixture before separation of the nitration mixture into the acid and organic phases.

Following the reconcentration step, the phase separation is carried out. This phase separation may take place at a markedly lower temperature than that used in the process disclosed in EP-A 597,361. This results in advantages from the safety engineering point of view. Furthermore, because of the reduced thermal loading, smaller quantities of by-products are obtained.

Because MNT is permitted in the reaction mixture, the reactor requirements for the process of the present invention are less exacting than those for known processes. The reactor no longer needs to be designed for complete conversion.

The residual quantity of MNT which is necessary to condense the exhaust vapors is achieved by conducting the reaction hypostoichio-metrically, or by reducing the acid concentration in the system. The solubility of the nitrated compounds, and hence the quantity of nitrated compounds in the acid circulation, is also reduced by reducing sulfuric acid concentration. Further, the acid need no longer be reconcentrated to as great an extent as in known processes after the reaction.

As a result of the incompletely conducted nitration in the process of the present invention, the quantity of nitrating acid may also be smaller. This results in a lower nitric acid load in the waste water.

A molar ratio of nitric acid to toluene greater than 2.5 does not make technical sense in the process of the present of the invention.

When the molar ratio of nitric acid to toluene is ≧2.0, MNT is still present in the nitration reaction mixture. The presence of MNT may be achieved, for example, by premature termination of the reaction or by incomplete mixing of the reaction components.

Having thus described our invention, the following Examples are given as being illustrative thereof. All percentages given in these Examples are percentages by weight.

EXAMPLES

Example 1

248 g/h (2.692 mol/h) toluene and 9424 g/h (5.384 mol/h) nitrating acid (composition: 77.0% by weight $H_2SO_4$: 3.6% by weight $HNO_3$; 19.4 wt % by weight $H_2O$) were each brought to a temperature of 120° C. and reacted in a tube reactor under adiabatic conditions. The reaction mixture which left the reactor at 160° C. contained 7.5% by weight mononitrotoluene and was placed under 30 mbar vacuum for reconcentration. The temperature of the bottom discharge was varied. The exhaust vapors leaving at the top were condensed at a cooling device, with the condensate running off as a fluid. The residual MNT content of the reaction mixture which was thus reconcentrated was:

110° C. 1.05%
115° C. 0.44%
120° C. 0.21%
125° C. 0.17%
130° C. 0.10% at the respective bottom temperatures shown.

Example 2

261 g/h (2.834 mol/h) toluene and 9424 g/h (5.384 mol/h) nitrating acid (same composition as in Example 1) were each brought to a temperature of 120° C. and reacted in a tube reactor under adiabatic conditions. The reaction mixture which left the reactor at 165° C. contained 13.6% mononitrotoluene and was placed under 30 mbar vacuum. The temperature of the bottom discharge during reconcentration was varied. The exhaust vapors leaving at the top were condensed at a cooling device, with the condensate running off as a fluid. The residual MNT content of the reaction mixture which was thus reconcentrated was:

100° C. 3.34%
115° C. 1.33%
120° C. 0.48%
125° C. 0.21%
130° C. 0.12%.

at the respective bottom temperatures shown.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:
1. A continuous, single-stage process for the production of a dinitrotoluene isomer mixture comprising
  A) reacting
    1) toluene with
    2) a nitrating acid composed of
      (a) from about 80 to about 100% by weight of inorganic constituents which include
        (i) from about 60 to about 90% by weight of sulfuric acid,
        (ii) from about 1 to about 20% by weight of nitric acid, and

(iii) at least 5% by weight of water, and
(b) from 0 to about 20% by weight of organic constituents which include
(i) at least 70% by weight dinitrotoluene isomers and
(ii) from 0 to 30% by weight by-products of the nitration process under adiabatic conditions in amounts such that the molar ratio of nitric acid to toluene is at least 1.5:1 and such that the ratio of mononitrotoluene to dinitrotoluene in the vapor condensate is from 10:1 to 1:5 and at least 5% by weight of mononitrotoluene, based on total weight of reaction product, remains in the reaction mixture, B) removing at least 5% by weight of water from the reaction mixture of A), C) removing the reaction mixture of B) at a temperature of at least 120° C., D) separating the reaction mixture from C) into an acid phase and an organic phase containing dinitrotoluene, E) recovering the dinitrotoluene from the organic phase separated in D).

2. The process of claim 1 in which the molar ratio of nitric acid to toluene in A) is about 1.8:1.

3. The process of claim 1 in which the water is removed in B) by flash evaporation.

4. The process of claim 1 in which the water is removed in B) by flash evaporation with simultaneous supply of heat.

5. The process of claim 1 in which the water is removed in B) by distillation.

6. The process of claim 1 in which up to 0.6 mole of 50–100% by weight nitric acid is added to the reaction mixture before step D).

7. The process of claim 1 in which up to 0.3 mole of 50–100% by weight nitric acid is added to the reaction mixture before step D).

8. The process of claim 1 in which up to 0.2 mole of 50–100% by weight nitric acid is added to the reaction mixture before step D.

9. The process of claim 1 in which 50–100% by weight nitric acid is added to the acid phase from D).

10. The process of claim 1 in which 50–100% by weight nitric acid added to the acid phase from D) and the resultant acid mixture is recycled to step A).

* * * * *